United States Patent
Götze et al.

(10) Patent No.: US 7,222,964 B2
(45) Date of Patent: May 29, 2007

(54) METHOD AND ARRANGEMENT FOR OPTICALLY STIMULATING THE VISUAL SYSTEM

(75) Inventors: Andreas Götze, Ilmenau (DE); Günter Henning, Ilmenau (DE); Peter Husar, Ilmenau (DE); Sebastian Berkes, Ilmenau (DE); Klaus Schellhorn, Ilmenau (DE); Falk Schlegelmilch, Ilmenau (DE)

(73) Assignee: Carl Zeiss Meditec AG, Jena (DE)

( * ) Notice: Subject to any disclaimer, the term of this patent is extended or adjusted under 35 U.S.C. 154(b) by 607 days.

(21) Appl. No.: 10/432,834

(22) PCT Filed: Nov. 21, 2001

(86) PCT No.: PCT/EP01/13477

§ 371 (c)(1),
(2), (4) Date: May 22, 2003

(87) PCT Pub. No.: WO02/41768

PCT Pub. Date: May 30, 2002

(65) Prior Publication Data

US 2004/0051848 A1    Mar. 18, 2004

(30) Foreign Application Priority Data

Nov. 22, 2000   (DE)   ................. 100 58 127
Aug. 21, 2001   (DE)   ................. 101 40 871
Sep. 20, 2001   (DE)   ................. 101 46 330

(51) Int. Cl.
*A61B 3/02* (2006.01)
(52) U.S. Cl. ...................... 351/242; 351/246
(58) Field of Classification Search ........... 351/244, 351/242, 246, 243, 239, 222
See application file for complete search history.

(56) References Cited

U.S. PATENT DOCUMENTS 3,172,404 A * 3/1965 Copenhaver et al. ....... 351/224

(Continued)

FOREIGN PATENT DOCUMENTS

DE       196 49 858 A 1       6/1998

(Continued)

OTHER PUBLICATIONS

German Search Report of German Priority Application No. 101 46 330.8 dated Oct. 26, 2001.

(Continued)

*Primary Examiner*—Hung Xuan Dang
(74) *Attorney, Agent, or Firm*—Patterson, Thuente, Skaar & Christensen, P.A.

(57) ABSTRACT

A method and device for optically stimulating the visual system during static perimetry and for objectively evaluating adequate stimulus-related electrophysiological and/or magnetophysiological quantities. Light stimuli with defined parameters derived from a predetermined correlation function and from the known intensity dependence of the excitation response amplitude are presented to the observer. The excitation responses contained in the ERG and/or in the EEG/MEG are detected and processed. These excitation responses are used to determine and topographically evaluate the local sensitivity of the visual system. In one embodiment, the light sources are fixed inside a perimeter, and the excitation responses are amplified and digitized by a device, which preferably comprises an ERG/EEG measuring system and an A/D converter. To this end, the device, for the purpose of evaluating, and the light sources, for the purpose of controlling, are connected to a controlling means, preferably to a PC provided with evaluation and control software.

14 Claims, 2 Drawing Sheets

U.S. PATENT DOCUMENTS

| | | | |
|---|---|---|---|
| 4,255,023 A | 3/1981 | House | |
| 5,319,398 A | 6/1994 | Weijland | |
| 5,461,435 A | 10/1995 | Rootzen et al. | |
| 6,022,107 A | 2/2000 | Kutschbach et al. | |
| 6,086,206 A | 7/2000 | Sutter | |

FOREIGN PATENT DOCUMENTS

| | | |
|---|---|---|
| DE | 196 49 858 C 2 | 5/1999 |
| DE | 198 55 848 A 1 | 6/2000 |
| DE | 199 61 323 A1 | 6/2001 |
| EP | 0 495 247 A1 | 12/1991 |
| JP | 05-146404 | 6/1993 |
| WO | WO 89/01757 | 3/1989 |
| WO | WO 94/24925 | 11/1994 |
| WO | WO 98/24364 | 6/1998 |
| WO | WO 00/40140 | 7/2000 |
| WO | WO 01/39659 A1 | 6/2001 |

OTHER PUBLICATIONS

International Search Report (PCT/EP01/13477) dated Apr. 4, 2002.
German Search Report of German Priority Application No. 101 40 871.4 dated Jul. 1, 2002.

* cited by examiner

METHOD AND ARRANGEMENT FOR OPTICALLY STIMULATING THE VISUAL SYSTEM

CROSS REFERENCE TO RELATED APPLICATIONS

This application claims priority to PCT Application designating the U.S. Ser. No. PCT/EP01/13477, filed on Nov. 21, 2001, incorporated herein by reference, which claims priority to German Application Nos. 100 58 127.7 filed Nov. 22, 2000, 101 40871.7 filed Aug. 21, 2001 and 101 46 330.8 filed Sep. 20, 2001, incorporated herein by reference.

FIELD OF THE INVENTION

The invention refers to a method and an apparatus for optically stimulating the visual system in accordance with the requirements of static perimeters, and for the objective evaluation of adequate stimulus-related electro- and/or magnetophysiological values.

PRIOR ART

Prior art stimulation systems of objective perimeters that use binary controlled light stimulators are known. To give an example, monofocal light markers of a defined intensity that light up briefly are used in perimeters in order to check the functionality of the visual system.

In newer systems, multifocal (i.e. simultaneous at more than one location) optical stimuli are used where the sequence of such stimuli is generally controlled by pseudo-random binary sequences usually referred to as m-sequences, MLS (Maximum Length Sequence) or PRBS (Pseudo Random Binary Sequence).

The disadvantage of the methods used so far is that the generated optical stimuli (whether they were generated mono- or multifocally) have a constant level of intensity during an examination.

Even though the m-sequences used that are shown individually (monofocally) appear as a random sequence to the subject, the subject's visual system recognizes the basic cycle (the time basis for the change of pattern) very quickly if they are shown simultaneously (multifocally). The recognition of a pattern in the stimulation method automatically leads to a the adaptation of the sensory system to this stimulus, which leads to a decrease in attention. This significantly decreases the reliability of the physiological values examined.

With such a stimulation modus, only absolute scotoma (complete local failure of the visual function) and a small number of strong relative scotoma (partial local failure of the visual function, decreased sensitivity) can be diagnosed reliably.

In order to objectively answer the question regarding the perception of a light impulse at a particular retinal location, the EEG (electroencephalogram) of the subject is analyzed and searched for the presence of a response to the impulse using objective criteria. This creates an objective topological examination result regarding visual function—but only for one level of intensity of the light impulses.

For the much more commonly occurring relative scotomas it is necessary to use several logarithmically graduated levels of light in order to topographically record locally occurring losses of sensitivity such as is commonly done in static perimeters.

Using conventional stimulation methods, the objectification of the static perimeter would result in an unacceptable lengthening of the examination time.

DESCRIPTION OF THE INVENTION

Progressing on from this prior art, the object of the invention is to identify a method that will make it possible to generate optimized optical impulses with respect to the signal theory that are adequate for the physiological sensory perception, and then check the perception function using electro- and/or magnetophysiological values.

According to the invention, the object is met by using graduated light intensities in order to stimulate the visual system optically and by determining the chronological sequence and the spatial pattern of the light impulses with respect to an objective proof of responses to the stimuli. The responses to the stimuli are analyzed by means of methods of signal processing and then objectively checked for their existence with the aid of a detection test.

In one advantageous embodiments [sic] of the invention, the light source emitting the optical stimulation is controlled such that graduated light intensities can be differentiated by physiological sensory perception. The result is amplified, digitized, and the put into an evaluation system, whereby appropriate evaluation logarithms are utilized in order to create the objective sensitivity profile of the visual field.

A subject is preferably shown a spatial pattern generated by at least two light impulses on a screen, whereby the sequence of light intensity of the impulses shown corresponds to a platinum sequence as discussed below. The subject's potential responses are recorded with the aid of an EEG or MEG (magnetoencephalogram) or an ERG (electroretinogram) measuring system, and upon analysis of these potential responses a conclusion is drawn regarding the functionality of the impulse localizations tested. The results can be used to topographically depict the functionality of the visual system.

The significant advantage of the methods according to the invention, lies in the fact that it is possible to determine the sensitivity profile of the visual field—as is common in static perimeters. This was not the case with the methods known heretofore. This way, a direct comparison of subjective and objective perimeter exam results can be made for the first time. The subjective perception of the light impulses presented can be assessed objectively using EEG/MEG and/or ERG analysis. Since the new process is completely automated, the strain on the patient is extremely low. Another advantage is a notable increase in functional diagnostic reliability arising from the elimination of patient error and errors made by the examining physician.

A further object of the invention is to provide an apparatus for performing the above-mentioned method, in which a planar or a curved screen is positioned in the visual field of the subject and upon which screen optical impulses with a defined chronological intensity sequence are generated at predetermined positions, preferably by means of light sources that have been arranged in a perimeter.

The light intensity, as well as the chronological sequence of the light impulse produced by the light sources, can be adjusted adequately throughout the area of physiological interest. Preferable the light sources are light emitting diodes.

Because of the sequence of light intensity corresponding to the platinum sequence, such an impulse modus presents to the subject a random spatial and time pattern for the visual system that is independent from the number of active light sources. Since the visual system can recognize neither a regular spatial pattern, nor a regular time pattern, adaptation—such as has been known from the past impulse sequences—an be eliminated. Thus possible acclimatization to the impulse and the resulting decrease in attention can be counteracted.

The basis for creating a platinum sequence is an m-sequence (MLS—Maximum Length Sequence) $s_1(n)$ of the length N. From this m-sequence, a second m-sequence $s_2(n)$ is created through decimation. In doing so, the periodically repeated initial sequence of each value is taken, where d and N must be relative prime. The calculation is done in accordance with the following rule:

$$s_2(n)=s_1(dn), \text{ where } d=2^k+1$$

and k such that r (order of sequence, $N=2^r-1$), divided by the largest common divisor of r and k, is odd and natural. By multiplying the two sequences by element, random product sequences $$s(n)=s_1(n)*s_2(n+u)$$

can be formed and be summarized with the initial sequences as a family of M=N+2 sequences. Here the following applies:

$$s_0(n) \in \{s_1(n), s_2(n), s_1(n)*s_2(n+u)\} \text{ where } 0 \leq u < N$$

The significant advantage compared to stimulation sequences used so far is that new information is constantly being given to the visual system by means of the intentional exclusion of subjectively perceptible patterns. This causes the readiness to perceive to constantly be maintained at a high level, and the examined physiological values have higher intensities than with the conventional methods.

BRIEF DESCRIPTION OF THE DRAWINGS

Below, the invention is described in greater detail using the drawings as a guideline. In that, FIG. 1 depicts a modular mimic display of the measuring position for the determination of the visual system's sensitivity profile.

DETAILED DESCRIPTION OF THE DRAWINGS

Figure 1:
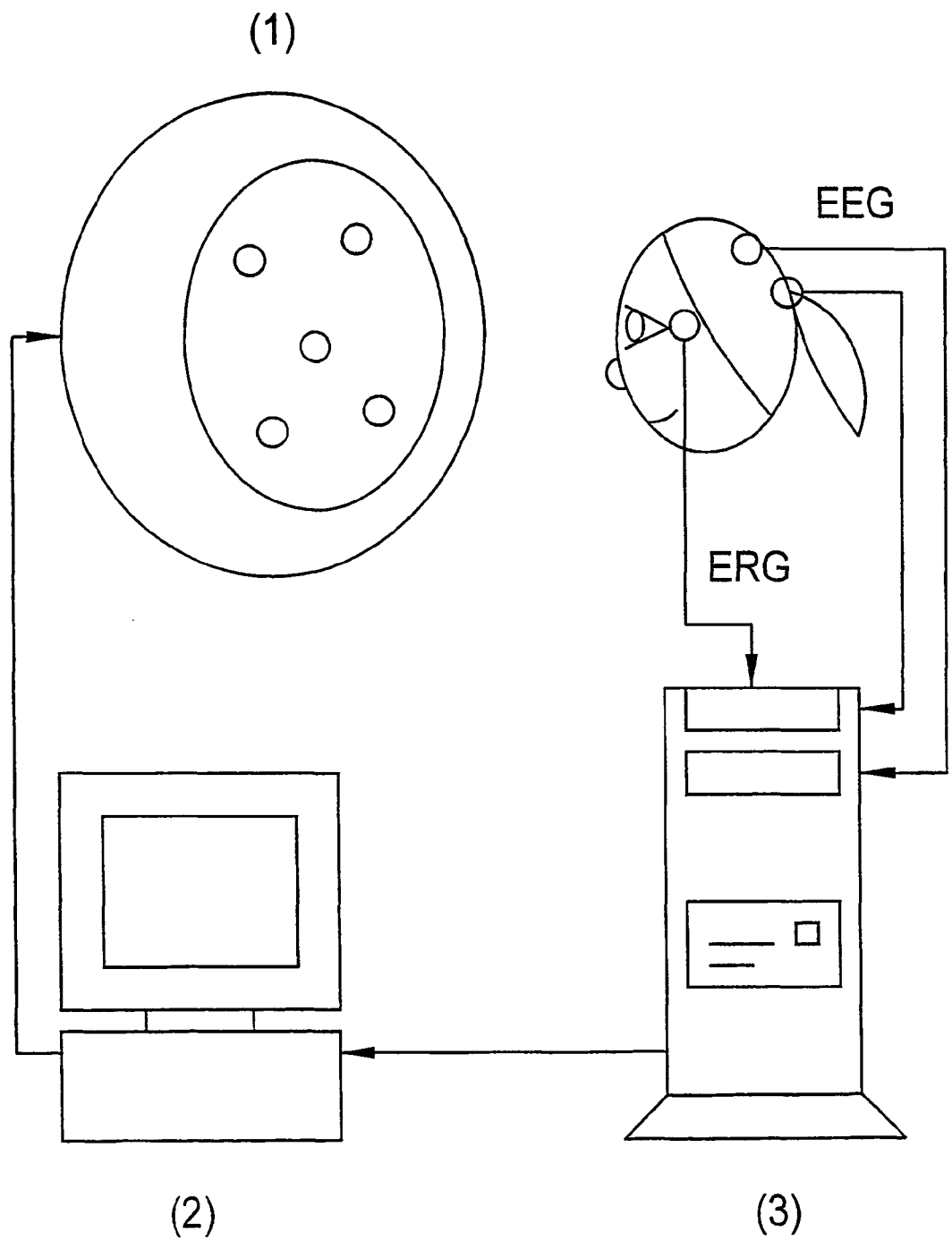

FIG. 1 depicts a symbolic patient sitting in front of a spherical projection screen such as a perimeter 1 in which light impulses of adequate intensity are generated at defined locations either by means of active light sources (LED—light emitting diodes) or using a projection system by means of a calibrated light source.

Figure 2:
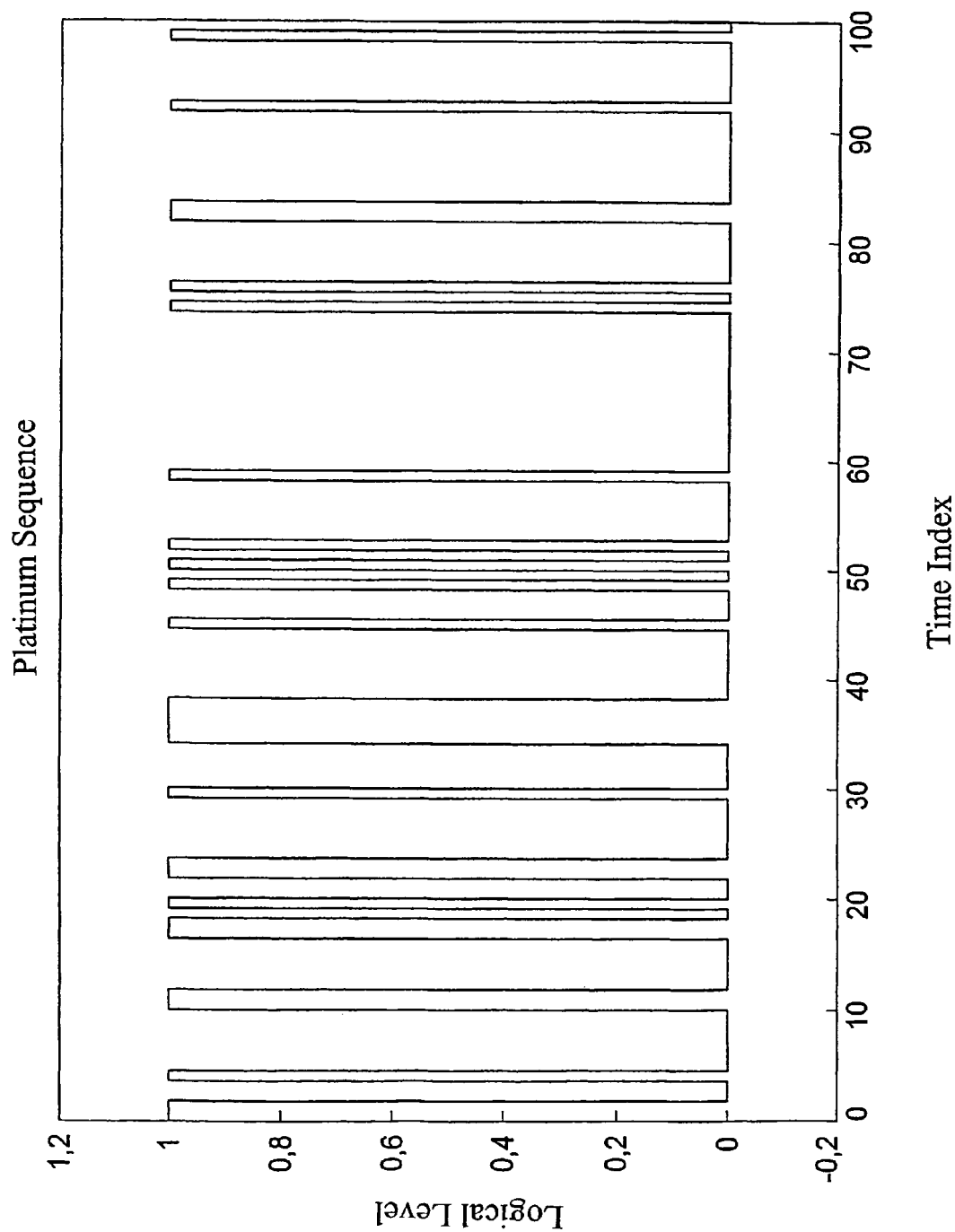
FIG. 2 depicts the example of an implemented platinum sequence.

These light sources are controlled by a control system 2, such as a PC with an appropriate software program, in such a way that the chronological sequence of intensity of the emitted light corresponds to the requirements of the signal theory and the physiology of perception of the generation requirement for platinum sequences (see FIG. 2). Such an optical impulse causes changes—also referred to as impulse responses—in the EEG/MEG. These responses are recorded, intensified, and digitized by an appropriate apparatus 3 that may comprise an ERG/EEG measuring system and an AD (analog to digital) converter. The digitized impulse responses are processed and analyzed in the control system 2.

As long as the LEDs light up individually, it is possible to subjectively answer the question as to whether or not they are seen by the patient if the patient cooperates. In order to significantly shorten the examination time, the LEDs are not controlled individually, but simultaneously. This kind of stimulation is referred to as multifocal stimulation. Here, a subjective evaluation of the responses to the impulses is no longer possible, and the control system 2 takes over the evaluation. Since it is known during evaluation in what sequence the individual impulse positions were triggered, each stimulation response belonging to each stimulation position can be calculated from the overall potential cortical and retinal responses.

We claim:

1. A method for stimulation of the visual system during a perimetric visual field examination, comprising the steps of
    stimulating the visual system with stimuli of graduated light intensity;
    determining the chronological sequence and spatial pattern of the light impulses based upon objectively measured impulse responses, and
    checking and analyzing the existence of impulse responses by means of signal processing methods.

2. The method according to claim 1, wherein the light source or sources are controlled such that graduated light intensities can be differentiated by physiological sensory perception.

3. The method according to claim 1, further comprising the steps of
    measuring EEG responses;
    digitizing measured EEG responses; and
    sending the results to an evaluation system.

4. The method according to claim 1, further comprising the step of determining the objective sensitivity profile of the visual field by the use of appropriate mathematical evaluation functions.

5. A method for the automated functionality exam of the visual system, comprising the steps of
    showing a subject a spatial pattern consisting of at least two light stimuli on a screen;
    sequentially varying a light intensity of the light stimuli, where the sequence of the light intensity of the stimuli shown corresponds to a platinum sequence;
    recording the subject's potential responses with a measuring system selected from a group consisting of an EEG, an MEG and an ERG
    evaluating the potential responses for information regarding the functionality of the stimulus localizations tested.

6. The method as claimed in claim 5, in which the platinum sequence further comprises;
    creating a first m-sequence $s_1(n)$ of length N;
    creating a second m-sequence $s_2(n)$ through decimation;
    taking the periodically repeated initial sequence of each value, where d and N are relative prime;
    performing a calculation in accordance with the following rule:

$$s_2(n)=s_i(dn),$$

where $d=2^k+1$ and k is such that r (order of sequence, $N=2^r-1$), divided by the largest common divisor of r and k, is odd and natural;
    multiplying the two sequences by element to form random product sequences to form $$s(n)=s_i(n)*s_2(n+u)$$

and
summarizing with the initial sequences as a family of M=N+2 sequences where the following applies:

$$s_0(n) \in \{s_1(n), s_2(n), s_1(n)*s_2(n+u)\} \text{ where } 0 \leq u < N.$$

7. An apparatus for stimulation of the visual system during a perimetric visual field examination, comprising:
a planar or curved screen positioned in a subject's field of vision;
a light source capable of producing stimuli of varying intensity and at predetermined locations forming a pattern proximate the screen;
a sequencer and spatial pattern generator that generate the stimuli in response to objectively measured physiological responses; and
a signal processor for analyzing and checking the physiological responses.

8. Apparatus according to claim 7, in which the
light sources are arranged in a perimeter and further comprising
amplification and digitization electronics by which the physiological responses to the stimuli are amplified and digitized.

9. Apparatus according to claim 7, in which
the amplification and digitization electronics comprise an ERG/EEG measuring system and an AD converter, connected to a personal computer loaded with an evaluation software for the purpose of performing an evaluation, and the light source is connected to the personal computer loaded with control software.

10. Apparatus according to claim 7, in which the light source comprises light emitting diodes.

11. An apparatus for stimulation of the visual system during a visual field examination, comprising:
a sensor for sensing neurological response to visual stimuli;
a signal processor in operable communication with the sensor for analyzing and checking the neurological responses;
a sequencer and spatial pattern generator in operable communication with the signal processor that generate the stimuli in response to the neurological responses; and
a light source controlled by the sequencer and spatial pattern generator to generate the stimuli in patterns and intensities as directed by the sequencer and spatial pattern generator responsive to the neurological responses sensed.

12. The apparatus as claimed in claim 11, in which the pattern and intensity of the stimuli vary in correspondence to a mathematical function.

13. The apparatus as claimed in claim 11, in which the pattern and intensity of the stimuli vary in correspondence to a platinum sequence.

14. The method as claimed in claim 13, in which the platinum sequence further comprises:
creating a first m-sequence $s_1(n)$ of the length N;
creating a second m-sequence $s_2(n)$ through decimation;
taking the periodically repeated initial sequence of each value, where d and N are relative prime;
performing a calculation in accordance with the following rule:

$$s_2(n) = s_1(dn),$$

where $d = 2^k + 1$
and k is such that r (order of sequence, $N = 2^r - 1$), divided by the largest common divisor of r and k, is odd and natural;
multiplying the two sequences by element to form random product sequences to form $$s(n) = s_1(n)*s_2(n+u)$$

and
summarizing with the initial sequences as a family of M=N+2 sequences where the following applies:

$$s_0(n) \in \{s_1(n), s_2(n), s_1(n)*s_2(n+u)\} \text{ where } 0 \leq u < N.$$

* * * * *